United States Patent
Turick et al.

(10) Patent No.: US 11,846,626 B2
(45) Date of Patent: Dec. 19, 2023

(54) ELECTROCHEMICAL DETECTION OF MICROBIAL STRESS

(71) Applicant: Savannah River Nuclear Solutions, LLC, Aiken, SC (US)

(72) Inventors: Charles E Turick, Aiken, SC (US); Charles E Milliken, Evans, GA (US); Hector Colon-Mercado, Aiken, SC (US); Scott D Greenway, Aiken, SC (US); Ariane L Martin, Sitka, AK (US)

(73) Assignee: Battelle Savannah River Alliance, LLC, Aiken, SC (US)

( * ) Notice: Subject to any disclaimer, the term of this patent is extended or adjusted under 35 U.S.C. 154(b) by 660 days.

(21) Appl. No.: 15/808,244

(22) Filed: Nov. 9, 2017

(65) Prior Publication Data

US 2019/0137475 A1     May 9, 2019

(51) Int. Cl.
| | |
|---|---|
| *G01N 27/30* | (2006.01) |
| *G01N 27/327* | (2006.01) |
| *G01N 33/483* | (2006.01) |
| *C12Q 1/02* | (2006.01) |
| *C12Q 1/04* | (2006.01) |

(52) U.S. Cl.
CPC ......... *G01N 33/4833* (2013.01); *C12Q 1/025* (2013.01); *C12Q 1/04* (2013.01); *G01N 27/301* (2013.01); *G01N 27/327* (2013.01); *G01N 2333/195* (2013.01)

(58) Field of Classification Search
CPC ............... C12M 1/00; G01N 2333/195; G01N 33/4833; G01N 27/301; G01N 27/327; C12Q 1/04

See application file for complete search history.

(56) References Cited

U.S. PATENT DOCUMENTS

| | | | |
|---|---|---|---|
| 4,983,516 A | 1/1991 | Turner et al. | |
| 5,312,590 A | 5/1994 | Gunasingham et al. | |
| 5,521,101 A | 5/1996 | Saini et al. | |
| 6,235,520 B1 | 5/2001 | Malin et al. | |
| 6,299,757 B1 | 10/2001 | Feldman et al. | |
| 6,649,402 B2 | 11/2003 | Van der Weide et al. | |
| 7,511,142 B2 | 3/2009 | Xie et al. | |
| 7,704,745 B2 | 4/2010 | Baudenbacher et al. | |
| 7,794,994 B2 | 9/2010 | Cranley et al. | |
| 9,175,408 B2 | 11/2015 | Lovel et al. | |
| 2004/0096927 A1 | 5/2004 | Chittock et al. | |
| 2006/0180479 A1 | 8/2006 | Sparkes et al. | |
| 2013/0096030 A1 | 4/2013 | Jeppesen et al. | |
| 2013/0309739 A1* | 11/2013 | Radtke | C10G 1/02 435/166 |
| 2014/0004578 A1 | 1/2014 | Bond et al. | |
| 2016/0333301 A1* | 11/2016 | Yau | C12M 1/42 |

FOREIGN PATENT DOCUMENTS

| | | |
|---|---|---|
| WO | WO 2003087293 | 10/2003 |
| WO | WO 2011000572 | 1/2011 |

OTHER PUBLICATIONS

A. Martin, Clemson University Thesis, Use of electrochemistry to monitor the growth and activity of clostridium phytofermentans, Dec. 2015. (Year: 2015).*
F. Leroy et al. Sugars relevant for sourdough fermentation stimulate growth of and bacteriocin production by Lactobacillus amylovorus DCE 471, 112 International Journal of Food Microbiology 2006, p. 102-11. (Year: 2006).*
A.L. Martin, In-situ electrochemical analysis of microbial activity, AMB Express, 2018, 8: 162, p. 1-10. (Year: 2018).*
Stress by Merriam-Webster (Year: 2021).*
Kinetics by Merriam-Webster (Year: 2021).*
Denis Andrienko, Cyclic Voltammetry, Jan. 22, 2008, 12 pages.
S. Venkata Mohan, S. Srikanth, M. Lenin Babu, P.N. Sarma, Insight into the dehydrogenase catalyzed redox reactions and electron discharge pattern during fermentative hydrogen production, Bioresource Technology 101, 2010, 8pages.
Derek R. Lovely, Powering microbes with electricity: direct electron transfer from electrodes to microbes, Environmental Microbiology Reports (2011) 3(1), Jul. 21, 2010, 9 pages.
Jorg S. Deutzmann, Merve Sahin, Alfred M. Spormann, Extracellular Enzymes.
Facilitate Electron Uptake in Biocorrosion and Bioelectrosynthesis, mBio, vol. 6, Issue 2 Mar./Apr. 2015, 8 pages.
Mark Shwartz, "Stanford scientists discover how microbes acquire electricity in making methane," Stanford Report, May 18, 2015.

* cited by examiner

*Primary Examiner* — Caitlyn Mingyun Sun
(74) *Attorney, Agent, or Firm* — Dority & Manning, P.A.

(57) ABSTRACT

The present invention is directed to a method of detecting microbial stress. The method comprises the following: providing an electrochemical device having at least one reference electrode and one working electrode wherein the electrochemical device also contains a fermenting microbe, setting an electrochemical potential, providing a source of electrical energy electrically connected to the at least one working electrode, detecting a transfer of electrons from the working electrode to the fermenting microbe, wherein the detection is an indication of microbial stress, and providing a remedial action in response to the indication of microbial stress.

13 Claims, 3 Drawing Sheets

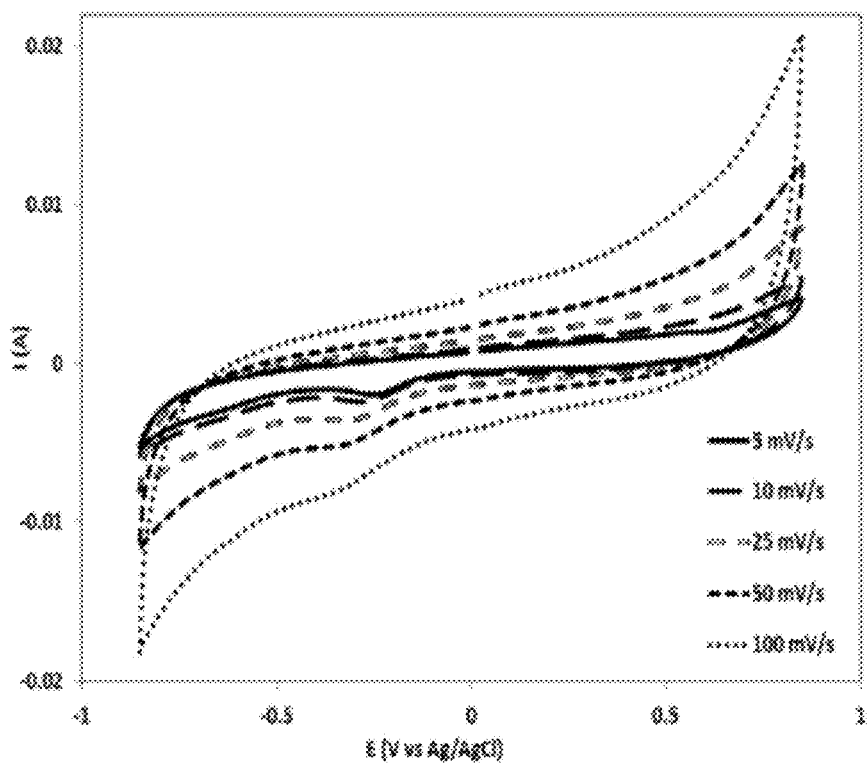
Figure 2
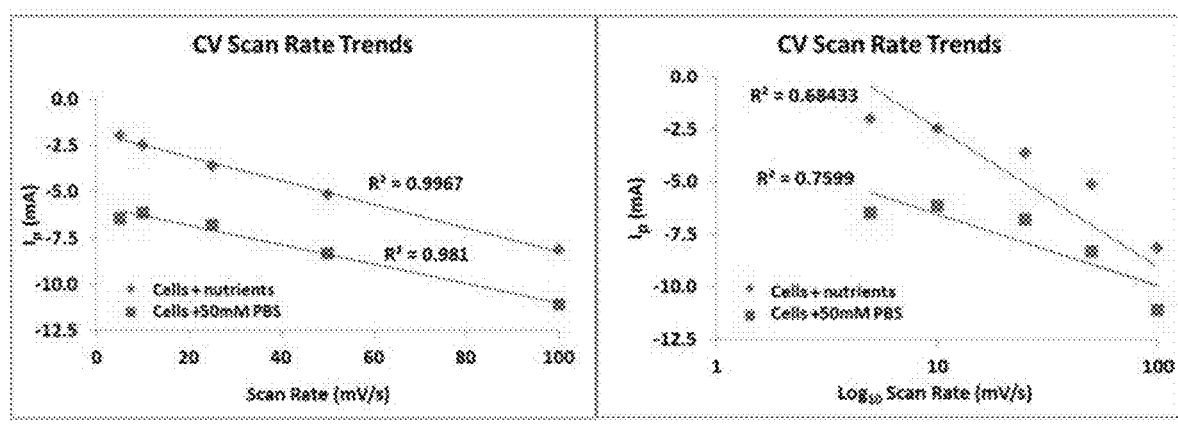
Figure 3a
Figure 3b

ELECTROCHEMICAL DETECTION OF MICROBIAL STRESS

FEDERAL RESEARCH STATEMENT

This invention was made with Government support under Contract No. DE-AC09-08SR22470, awarded by the U.S. Department of Energy. The Government has certain rights in the invention.

BACKGROUND OF THE INVENTION

Bioprocesses are commonly employed for the production of fuel and energy. Fermentation can be used for the production of microbial metabolites such as alcohols (i.e. ethanol), acetate (i.e. vinegar), associated with fuels, chemicals, and foods. Fermentation involves the breakdown of organic carbon through chemical reactions that involve electron flow. The rate of electron flow in microbial systems can be impeded in several ways. A decrease or absence of an organic carbon source can decrease or stop electron flow which can relate to growth. Electron flow can also be impeded by the buildup of metabolic end products that could inhibit microbial activity thereby potentially inactivating the microbes and ending the process.

In many cases, this is a desired reaction because the end products are microbial wastes but are regarded as useful products such as foods (e.g., yogurt, sauerkraut, wine and beer, etc.), chemicals (e.g., ethanol, butanol, acetate, etc.), and pharmaceuticals (e.g., antibiotics). These types of fermentation often require pure cultures and must be monitored to know when activity stops. In the event of contamination, these microbial processes do not proceed as desired and may not stop at the desired end product, thereby reducing the product yield. In the case of contamination by pathogenic microbes, food poisoning can result. On-line methods to follow the microbial activity during these processes will assist in a higher degree of quality control at low cost.

A more complex process involves industrial methane production where very diverse, mixed cultures convert waste organics sequentially to methane and carbon dioxide. This complex conversion process relies on a multifaceted chain of events to convert large organic molecules (e.g., cellulose) to smaller molecules, ultimately to methane and carbon dioxide. A lack of organic carbon, chemical inhibitors present in waste organics, or an unpredicted buildup of microbial wastes could slow or stop microbial activity. On-line monitoring methods will also benefit this industry as well by providing low cost real time information about the stability and efficiency of the system.

In general, fermentation is a metabolic process that can occur in microbes, such as yeast and bacteria, wherein sugar is converted to other molecules such as acids, gases, and/or alcohols. Typically, glucose is converted via a metabolic pathway to an organic molecule, such as acetate, formate, or pyruvate, using a coenzyme, such as the oxidized form of nicotinamide adenine dinucleotide ($NAD^+$) which is required for energy to drive metabolic activity. During this process, $NAD^+$, as the oxidizing agent, accepts electrons from other molecules or sources and becomes reduced to form NADH, which can then be used as a reducing agent to donate electrons.

In certain instances, however, intracellular electron flow is impeded and as a result microbes are starved of electrons thereby inhibiting the progression of the metabolic pathway. Typically, in order to determine whether the microbes are stressed (or starved of electrons), periodic samples must be removed, processed, analyzed and evaluated. The sample can provide an indication as to the manner in which the process is operating. However, such methods can be quite labor intensive and time consuming. As a result, the frequency of the sampling may be limited which can then affect the efficiency of the operation. Additionally, current methods cannot be employed in a timely and cost effective manner to prevent these imbalanced conditions from occurring. For instance, bioremediation may not even be implemented until it is known that an unbalanced condition exists.

As a result, there is a need for an improved method of monitoring the physiological status of microbes, in particular for determining whether an imbalanced condition may exist and thereby allowing for a resolution. In this regard, such method could be more energy-efficient and economical than conventional methodologies.

SUMMARY OF THE INVENTION

Aspects and advantages of the invention will be set forth in part in the following description, or may be apparent from the description, or may be learned through practice of the invention.

In accordance with one embodiment of the present invention, a method of detecting microbial stress. The method comprises the following: providing an electrochemical device having at least one reference electrode and one working electrode wherein the electrochemical device also contains a fermenting microbe, setting an electrochemical potential, providing a source of electrical energy electrically connected to the at least one working electrode, detecting a transfer of electrons from the working electrode to the fermenting microbe, wherein the detection is an indication of microbial stress, and providing a remedial action in response to the indication of microbial stress.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1b is an enlarged view of the peaks of the cyclic voltammogram of FIG. 1a.

FIG. 2 provides cyclic voltammograms conducted at different scan rates.

FIG. 3a provides linear fits of the peak current as a function of the scan rate.

FIG. 3b provides linear fits of the peak current as a function of the scan rate.

DETAILED DESCRIPTION OF THE INVENTION

Figure 1A:
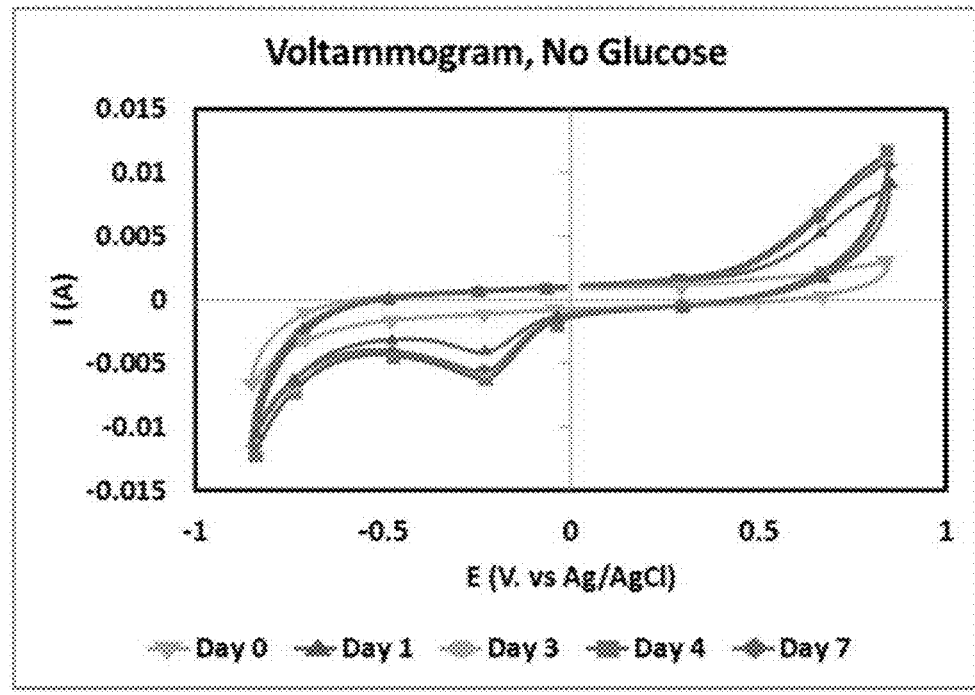
FIG. 1a is a cyclic voltammogram of a bacterial suspension without the presence of glucose.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, one embodiment of the present invention is directed to a method of monitoring the physiological status of microbes. In particular, one embodiment of the present invention is directed to a method of detecting microbial inhibition. In particular, the method disclosed herein employs electrochemical means for monitoring and detecting. Such methods can be employed to determine whether an imbalanced condition may exist that can result in microbial stress. For instance, these may include, but are not limited to a lack of feed stock, which may typically serve as the electron donor or source of electrons, or the presence of a chemical inhibitor. Upon determining the presence of an imbalanced condition (or microbial stress), a resolution or remedy may be implemented. Thus, the method of the present invention can provide opportunities to maintain strict process control by checking for changes quickly and/or continuously.

In general, the microbes of the present invention are fermenting microbes. In addition, these microbes may also be referred to as anaerobic microbes or facultative anaerobes that do not require oxygen for undergoing various metabolic processes.

In one embodiment, the microbes are of the domain Bacteria. In one particular embodiment, the microbes include, but are not limited to, those of the phyla Cyanobacteria, Fermicutes, Proteobacteria in the Alpha, Beta, Gamma, Delta and Epsilon subclasses, etc. In this regard, the microbes include gram-negative bacteria and gram-positive bacteria. However, it should be understood that the phyla, including the respective genera and/or species, are not necessarily limited.

During the fermentation process, the fermenting microbes convert an energy source into other molecules such as acids, gases, and/or alcohols. The energy source is not necessarily limited and may he any source of organic carbon that can be converted by the fermenting microbes. For instance, the energy source, as just one example, can be a sugar. In general, a sugar is a short-chain soluble carbohydrate and can include a monosaccharide and/or a disaccharide. In one particular embodiment, the sugar is a monosaccharide. Monosaccharides include, but are not limited to, glucose, fructose, and galactose. In one further particular embodiment, the energy source can be glucose. In one embodiment, the energy course can be waste, such as agricultural waste, food waste, etc. In one embodiment, the energy course can be cellulosics, starches, proteins, lipids, etc.

In this regard, in one embodiment, the energy source is one that is added to the fermentation process. Accordingly, in one embodiment, the electrodes may not serve as an energy source or the main energy source. Instead, the electrons of the electrodes may simply be used to detect the presence of microbial stress. Accordingly, the main source of electrons for remedial action when the microbes are starved of an energy source is from the organic carbon energy source.

Typically, the energy source is converted via a metabolic pathway to an organic molecule using a coenzyme. As an example, glucose can be converted via a metabolic pathway to an organic molecule, including but not limited to acetate, formate, or pyruvate, using a coenzyme, such as the oxidized form of nicotinamide adenine dinucleotide ($NAD^+$). In one particular embodiment, the metabolic process is employed to produce acetate. In another particular embodiment, the metabolic process is employed to produce formate. In another particular embodiment, the metabolic process is employed to produce pyruvate.

During this process, $NAD^+$, as the oxidizing agent, accepts electrons from other molecules or sources and becomes reduced to form NADH, which can then be used as a reducing agent to donate electrons. Thus, the electron shuttle nicotinamide adenine dinucleotide (NAD) carries electrons from one reaction center to another.

In certain instances, however, microbes are starved of electrons thereby inhibiting the progression of the metabolic pathway. For instance, during imbalanced conditions, the oxidized form ($NAD^+$) generally has a higher concentration than the reduced form (NADH). However, in certain situations, these "electron starved" microbes can accept extracellular electrons from an external source when present that serves as a source of electrons. Thus, the external source can serve as the electron donor and the microbe, in general, serves as the electron acceptor. In essence, the microbes are in electron communication with the electrode. Once the electrons are transferred to the microbes, complete electron flow can be accomplished within the microbe.

In such instance, these microbes can be referred to as electrotrophs because of their ability to directly accept electrons rather than relying solely on electron shuttles or intracellular hydrogen oxidation for such electrons. In other words, because of such direct electron transfer, the present invention does not require another molecule to shuttle electrons between the electrodes and the microbes. This concept of direct electron transfer from electrodes to microbes is discussed in 'Power microbes with electricity: direct electron transfer from electrodes to microbes," Environmental Microbiology Reports (2011), 3(1), 27-35, 2010 and U.S. Pat. No. 9,175,408, both of which are incorporated herein by reference in its entirety.

Electrons can be transferred to the microbes using any method generally known in the art. For instance, according to one method, an electrochemical device containing at least one electrode may be employed. In general, the device can be controlled and/or monitored using a controller, such as a potentiostat. In this regard, the electrochemical device, including the electrodes, is electrically connected to the controller.

In general, the electrochemical device contains at least one electrode. In one embodiment, the electrochemical device comprises at least two electrodes. In one particular embodiment, the electrochemical device comprises at least three electrodes. The electrodes can include a working electrode, a counter electrode, and/or a reference electrode. In one embodiment, the electrochemical device includes a working electrode and a counter electrode. In one embodiment, the counter electrode may also function as a reference electrode.

The electrodes can be made of any material generally employed in the art. In addition, the electrodes can be any convenient shape or size and may be physically oriented in any convenient orientation relative to each other. In addition, the electrodes may be made using any method generally known in the art.

In one embodiment, the electrodes may be conductive. In particular, in one embodiment, the electrode comprises a conductive carbon. In another embodiment, the electrode comprises a metal. The electrodes can include, but are not limited to, carbon paper, carbon cloth, carbon felt, carbon wool, carbon foam, graphite, porous graphite, graphite powder, a conductive polymer, platinum, palladium, titanium, gold, silver, nickel, copper, tin, iron, cobalt, tungsten, stainless steel, and combinations of these. In one embodiment, the electrode comprises graphite. In one embodiment, the electrode comprises a metal wherein the metal is selected from the group consisting of platinum, palladium, titanium; gold, silver, nickel, copper, tin, iron, cobalt, tungsten, stainless steel, etc. The working electrode and/or the counter electrode may comprise any of the aforementioned materials. In one embodiment, the reference electrode may be a normal hydrogen electrode, Ag/AgCl electrode, calomel electrode, etc. In one particular embodiment, the reference electrode may be an Ag/AgCl electrode. However, it should be understood that the working electrode, counter electrode, and/or the reference electrode may be any material as generally known in the art.

In addition, the electrochemical device may also include an electrolyte. The electrolyte may be any having properties that are compatible with the electrodes and other components present within the electrochemical device. In one embodiment, the electrolyte may be an aqueous based electrolyte. The aqueous solution may contain a salt at a concentration that supports the physiological function of the fermentation process and also provides a conducive environment for such process.

In general, the controller, such as the potentiostat, maintains the potential of the working electrode at a constant level with respect to the reference electrode by adjusting the current at the counter electrode. In this regard, the reference electrode establishes the electrical potential against which other potentials may be measured and the working electrode is where a cell reaction can take place. Additionally, the counter electrode is the electrode in which an electric current is expected to flow.

The potential may be set according to means and any value known in the art. For instance, the potential may be from −5 V to 5 V, such as from −3 V to 3 V, such as from −2 V to 2 V, such as from −1 V to 1 V.

The potentiostat may be employed to provide a source of electrical energy and can be electrically connected to an electrode. Ordinarily, the microbes will have a sufficient amount of energy source and electrons in order to continue with the metabolic process. However, in certain situations, the microbe may be stressed, for instance due to an imbalanced condition. For instance, there may be a redox imbalance within a microbe. In this situation, the microbe may not have the necessary electrons for continuing with a metabolic process. Or, alternatively, while electrons may be present, there may not be present in an amount sufficient for undergoing the process in an efficient manner.

As a result, it is believed that the microbes will obtain electrons from the electrode. In particular, in one embodiment, the electrons are transferred directly from the electrode to the microbe without the need of a shuttle. In general, the size of the electrode may distance the amount of electrons that are provided to the microbes. During such transfer, it is believed that the current produced from this activity can be proportional to the degree of starvation of the microbes. Thus, when an increase in the current is detected, an imbalanced condition is present because of the need of the microbes to extract electrons from an external source, rather than utilizing those available internally. In this regard, the current can be monitored and detected thereby quantifying a degree of inhibition. Essentially, the method of the present invention provides for an in situ analysis.

Essentially, a potential is set so that the electrons are poised to flow out of the electrode. Such potential may be referred to as a reducing potential. In this regard, the electrons can have a negative charge so that they "reduce" the charge of things they may react with. Thus, if the electrons are available and the bacteria want to take electrons from the electrode, an indication of microbial stress can be detected by observing an increase in the electrons leaving the electrode (i.e., observing the current).

When an imbalanced condition exists, it is important to address the condition. Generally, fermenting bacteria can be employed to supply food for other processes. If the fermenting microbes are not performing well, the process can become inefficient. Thus, the present invention can be employed to monitor the health of the microbes and remedy the situation so that the fermentation process can occur efficiently and effectively. In this regard, the present invention also provides a step of maintaining the microbes in order to keep them alive. In essence, the present invention provides conditions effective for the microbe to metabolize the energy source and/or continue the metabolic process.

These imbalanced conditions include, but are not limited to, electron starvation, insufficient energy source, non-optimum growth temperature, addition of air or oxygen, build-up of hydrogen, etc.

These conditions can be remedied by various methods known in the art. For instance, they can be remedied by providing an energy source, correcting the temperature, purging with nitrogen, etc.

In this regard, once the imbalanced condition is addressed, it may be observed that the current has diminished. For instance, by addressing the condition and a cause of the microbial stress, the decrease in the current can indicate a reduction in the transfer of the electrons from the electrode to the fermenting microbe.

Generally, when electrons are produced internally through the various metabolic processes within the microbes, the microbes will not seek electrons from an external source, such as the electrodes disclosed herein because intracellular electron flow has been restored to the microbes. As a result, when the microbes are not under stress, a current may not be detected because there will not be any transfer of electrons from the electrode to the microbe. Thus, the reduction in current can signal that the metabolic processes within the microbes are occurring in a natural manner without the need for the external source.

The current measurements can be collected using any method known in the art. For instance, the current can be measured or obtained from the controller, such as the potentiostat, and a software program. Initially, the background current (i.e., current of the working electrode in the absence of the microbes) can be determined and subtracted from the measurements obtained in the presence of the microbes in order to determine the current resulting from electron transfer to the microbes.

As a result, employing the method disclosed herein has many advantages. For instance, the detection of microbial stress can be performed in situ. That is, there is no need for periodic sampling of the system in order to determine in microbial stress is present. In addition, because it can be performed in situ, if microbial stress is detected, a cause of the stress can be addressed immediately. By addressing the cause in such a manner, the fermentation process can then be allowed to continue unimpeded.

The method and system disclosed herein can be beneficial for many applications. For instance, the method and system can be employed in industrial bioprocesses where fermenting microbes are employed to convert organic feed stock to value added chemicals, fuels, pharmaceuticals, or food. The method and system may also be employed for the destruction of wastes or contaminants. In one particular embodiment, the method may be employed in bioreactors, such as methane producing bioreactors. The resulting methane can be employed as a fuel for heating, transportation, cooking, and/or generating electricity.

The present disclosure may be better understood with reference to the following examples.

EXAMPLES

Example 1

Cyclic voltammetry was employed to evaluate the electrochemical activity of bacteria in suspension. The minimum concentration was about $10^4$ cells/mL. The potential was cycled from +1 V to −1 V at a scan rate of from 5-100 mV/s. The physiological conditions were suitable for growth such that there were sufficient electrolytes for solution conductivity to support electrochemical analysis.

In general, cyclic voltammograms provide oxidation peaks and concomitant reduction peaks. As illustrated in FIG. 1a, only reduction peaks (pointing down) were observed. Thus, the absence of oxidation peaks around the same potential indicates that the electrons are being consumed intracellularly. In general, the height of the peaks corresponds to the current drawn in (electrons consumed) by the cells.

Figure 1B:
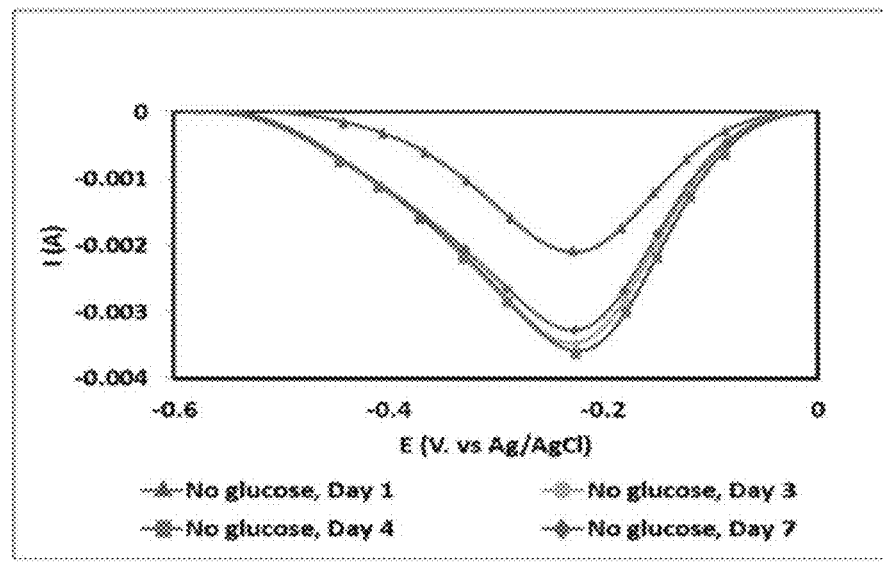

FIG. 1b provides an enlarged view of the reduction peaks of FIG. 1a. It was observed that, by day 7, the cells were metabolically inactive.

Example 2

The cells were removed from the growth solution of Example 1 and resuspended in a sterile 50 mM phosphate buffered saline solution. By doing so, the cells were separated from the nutrient solution and this could identify the cause of the reduction peaks in the cyclic voltammograms The potential was cycled from +1 V to −1 V at varying scan rates as identified in FIG. 2. These scan rates at 5 mV/s, 10 mV/s, 25 mV/s, 50 mV/s, 100 mV/s.

It was determined that the cell-free, spent nutrient solution did not demonstrate any reduction peaks while the resuspended cells in the buffered saline solution did illustrate the reduction peaks. As a result, it was determined that the electrochemical activity was associated with the surface of the cells rather than through the solution.

FIGS. 3a and 3b provide a linear fit of the peak current based on the scan rate. In particular, FIG. 3 is a function of the scan rate while FIG. 3b is a function of the log(10) of the scan rate. As indicated by the figure, the results further support that the electron transfer was to the bacteria and not associated with the bulk phase. For instance, FIG. 3a demonstrates a good linear fit of the data. If the electron transfer was from the solution, the data of FIG. 3b generally would have shown a better fit when log transformed.

Example 3

Figure 4:
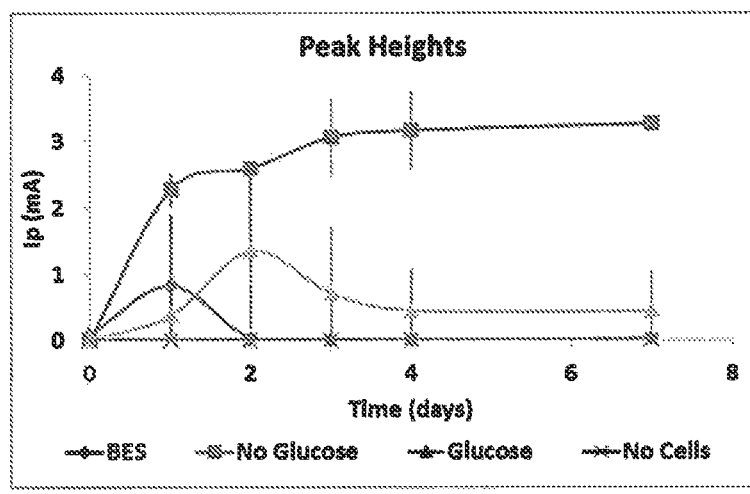
FIG. 4 provides the peak heights on each day for the various conditions.

FIG. 4 illustrates the peak heights of cyclic voltammograms under various conditions. For instance, scans were performed without cells but with glucose, with cells but without glucose, with cells and with glucose, and acidified to a pH of 3 with cells in the presence of 2-bromoethanesulphoate. The cell density was about $10^7$-$10^8$ cells/ml. Generally, this was a typical growth medium for methanogenic consortia, buffered isotonic conditions, vitamins, minerals, and glucose.

In this study, peak heights were evaluated and plotted as a function of time. As illustrated, the cells exposed to the 2-bromoethanesulphonate did not survive. Additionally, a current was not detected in the sample without cells. For the sample with glucose, a normal growth condition was observed. That is, some inhibition was observed around day 2 due to a temporary increase of hydrogen. Meanwhile, for the sample without glucose, a current was detected. Without glucose, the cells were stressed as determined by the increase in the current heights.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

The invention claimed is:

1. A method of detecting microbial stress, the method comprising
    providing an electrochemical device having at least one reference electrode and at least one working electrode wherein the electrochemical device also contains a fermenting microbe,
    setting an electrochemical potential,
    providing a first source of organic carbon to the fermenting microbe,
    providing a source of electrical energy electrically connected to the at least one working electrode,
    detecting a microbial stress by the transfer of electrons from the at least one working electrode to the fermenting microbe wherein the microbial stress is a result of electron starvation due to a lack of the first source of organic carbon and wherein the transfer of electrons is indicated by the presence of only a reduction peak in a cyclic voltammogram, and
    providing a remedial action in response to the microbial stress and detecting a decrease in the transfer of electrons from the at least one working electrode wherein the remedial action includes providing a second source of organic carbon.

2. The method of claim 1, wherein the fermenting microbe is of a domain Bacteria.

3. The method of claim 1, wherein the fermenting microbe comprises gram positive bacteria.

4. The method of claim 1, wherein the fermenting microbe comprises gram negative bacteria.

5. The method of claim 1, wherein the fermenting microbe comprises Cyanobacteria, Firmicutes, or Proteobacteria.

6. The method of claim 1, wherein the electrons are directly transferred from the at least one working electrode to the microbe.

7. The method of claim 1, wherein the organic carbon comprises agricultural waste or food waste.

8. The method of claim 1, wherein the organic carbon comprises agricultural waste or food waste.

9. (Withdrawn, Currently Amended) The method of claim 1, wherein the microbial stress is further due to a build-up of oxygen.

10. (Withdrawn, Currently Amended) The method of claim 1, wherein the microbial stress is further due to a build-up of hydrogen.

11. (Withdrawn, Currently Amended) The method of claim 1, wherein the remedial action further comprises a step of purging the electrochemical cell with nitrogen gas.

12. The method of claim 1, wherein the remedial action further comprises a step of changing a temperature.

13. The method of claim 1, wherein the decrease in the transfer of electrons is an indication of a reduction in microbial stress.

* * * * *